United States Patent [19]

Palameta et al.

[11] 4,381,304
[45] Apr. 26, 1983

[54] 4,9-DIHYDRO-4,9-DIOXO-1H-CYCLOHEPTA[B]PYRIDINE DERIVATIVES

[75] Inventors: Bozidar Palameta, Dollard des Ormeaux; Tibor Bogri, St. Laurent; Jehan Bagli, Kirkland, all of Canada

[73] Assignee: Ayerst, McKenna & Harrison, Inc., Montreal, Canada

[21] Appl. No.: 295,179

[22] Filed: Aug. 21, 1981

[51] Int. Cl.³ .................. C07D 221/04; A61K 31/435
[52] U.S. Cl. ..................................... 424/256; 546/183; 560/125
[58] Field of Search .................. 424/256; 546/183

[56] References Cited
PUBLICATIONS

Hayman, J. Biol. Chem., 240, 877 (1965).

Primary Examiner—Mark L. Berch
Attorney, Agent, or Firm—Arthur E. Wilfond

[57] ABSTRACT

Aldose reductase inhibitors of the formula

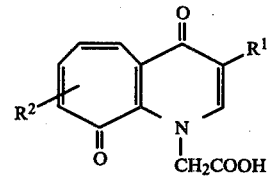

in which $R^1$ is COOH and $R^2$ is hydrogen, 8-halo or 6-hydroxy, or $R^1$ is $CON(R^3)$-$CH_2COOH$ wherein $R^3$ is lower alkyl and $R^2$ is hydrogen or 8-halo are useful for treating diabetic complications.

10 Claims, No Drawings

4,9-DIHYDRO-4,9-DIOXO-1H-CYCLOHEPTA[B]PYRIDINE DERIVATIVES

RELATED APPLICATIONS

Related hereto is U.S. patent application Ser. No. 295,180, filed on the same date as this application.

This application relates to cyclohepta[b]pyridine derivatives. More specifically, this application relates to 4,9-dihydro-4,9-dioxo-1H-cyclohepta[b]-pyridine-1-acetic acid derivatives and therapeutically acceptable salts thereof, to a process for their preparation, to pharmaceutical compositions thereof, and to methods for using the derivatives. The derivatives have pharmacologic properties which render them beneficial for the treatment of diabetes mellitus and associated conditions.

For many years diabetes mellitus has been treated with two established types of drugs, namely insulin and oral hypoglycemic agents. These drugs have benefited hundreds of thousands of diabetics by improving their well-being and prolonging their lives. However, the resulting longevity of diabetic patients has led to complications such as neuropathy, nephropathy, retinopathy, cataracts, and atherosclerosis. These complications have been linked to the undesirable accumulation of sorbitol in diabetic tissue, which in turn result from the high levels of glucose characteristic of the diabetic patient.

In mammals, including humans, the key enzyme involved in the conversion of hexoses to polyols (the sorbitol pathway) is aldose reductase. J. H. Kinoshita and collaborators, see J. H. Kinoshita, et al., Biochem. Biophys. Acta., 158, 472 (1968) and references cited therein, have demonstrated that aldose reductase plays a central role in the etiology of galactosemic cataracts by effecting the conversion of galactose to dulcitol (galactitol) and that an agent capable of inhibiting aldose reductase can prevent the detrimental accumulation of dulcitol in the lens. Furthermore, a relationship between elevated levels of glucose and an undesirable accumulation of sorbitol has been demonstrated in the lens, peripheral nervous cord and kidney of diabetic animals, see A. Pirie and R. van Heyningen, Exp. Eye Res., 3, 124 (1964); L. T. Chylack and J. H. Kinoshita, Invest. Ophthal., 8, 401 (1969) and J. D. Ward and R. W. R. Baker, Diabetol., 6, 531 (1970).

1,3-Dioxo-1H-benz[de]isoquinoline-2(3H)-acetic acid has been reported to be an effective inhibitor of aldose reductase, see D. Dvornik et al., Science, 182, 1146 (1973), and to be useful for the treatment of diabetic complications such as diabetic cataracts, neuropathy, nephropathy and retinopathy, see K. Sestanj, N. Simard-Duquesne and D. M. Dvornik, U.S. Pat. No. 3,821,383, June 28, 1974. (S)-6-Fluoro-2,3-dihydrospiro(4H-1-benzopyran-4,4'-imidazolidine)-2',5'-dione(-sorbinil) is still another compound that has received attention because of its aldose reductase inhibiting properties, see M. J. Peterson et al., Metabolism, 28 (Suppl. 1), 456 (1979). Accordingly, these compounds represent an important new approach for the treatment of diabetes mellitus.

The present application discloses novel cyclohepta[b]pyridine derivatives, which are effective inhibitors of aldose reductase. Furthermore, these new derivatives are structurally quite different from the above noted aldose reductase inhibitors. Related prior art compounds, on a structural basis, are a group of cyclohepta[b]pyridine-2-carboxylic acid derivatives, reported by J. F. Bagli and T. Bogri in U.S. Pat. No. 4,130,649, issued Dec. 19, 1978. Another group of related compounds are 4,6-dihydroxy-7-oxo-7H-cyclohepta[b]pyridine-3-carboxylic acid derivatives reported by R. Slack and C. F. Attridge, Chemistry and Industry, 471 (1952) and by K. Yamane, see Chem. Abstr., 56, 448b (1962) for Nippon Kagaku Zasshi, 81, 295 (1960). The prior art compounds are distinguished from the present compounds by the nature of the substituents on the cyclohepta[b]pyridine ring system and by different pharmacologic properties.

SUMMARY OF THE INVENTION

The cyclohepta[b]pyridine derivatives of this invention are represented by formula I

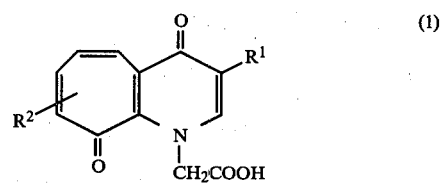

in which $R^1$ is COOH and $R^2$ is hydrogen, 8-halo or 6-hydroxy, or $R^1$ is $CON(R^3)$—$CH_2COOH$ wherein $R^3$ is lower alkyl and $R^2$ is hydrogen or 8-halo; or a therapeutically acceptable salt thereof with an organic or inorganic base.

A preferred group of the compounds is represented by formula I in which $R^1$ is COOH and $R^2$ is hydrogen, 8-halo or 6-hydroxy, or $R^1$ is $CON(CH_3)$—$CH_2COOH$ and $R^2$ is hydrogen, or a therapeutically acceptable salt thereof with an organic or inorganic base.

A most preferred group of compounds is represented by formula I in which $R^1$ is COOH and $R^2$ is hydrogen, 8-bromo or 6-hydroxy, or a therapeutically acceptable salt thereof with an organic or inorganic base.

The compounds of formula I can be prepared by a process described hereinafter.

A method is provided for preventing or relieving diabetes mellitus associated complications in a diabetic mammal by administering to said mammal a prophylactic or alleviating amount of the compound of formula I or therapeutically acceptable salt thereof with an organic or inorganic base. These complications include neuropathy, nephropathy, retinopathy and cataracts.

The compound of formula I, or a therapeutically acceptable salt thereof with an organic or inorganic base, when admixed with a pharmaceutically acceptable carrier, forms a pharmaceutical composition which can be used according to the preceding method.

DETAILED DESCRIPTION OF THE INVENTION

The term "lower alkyl" as used herein means a straight chain alkyl radical containing from one to six carbon atoms, preferably one to two carbon atoms, or a branched chain alkyl radical containing three to four carbon atoms and includes methyl, ethyl, propyl, 1-methylethyl, propyl, 2-methylpropyl and 1,1-dimethylethyl.

The term "halo" as used herein means a halo radical and includes fluoro, chloro, bromo and iodo.

The term "lower alkanol" as used herein means both straight and branched chain alkanols containing from one to four carbon atoms and includes methanol, ethanol, isopropanol, butanol and the like.

The term "inorganic proton acceptor" as used herein means the inorganic bases, preferably the alkali metal hydrides, hydroxides and carbonates, or their corresponding lower alkoxides, for example, sodium hydride, potassium, hydroxides, sodium carbonate, potassium carbonate, sodium ethoxide and the like.

The term "organic proton acceptor" as used herein means the organic bases or amines, for instance, triethylamine, pyridine, N-ethylmorpholine, 1,5-diazabicyclo[4.3.0]non-5-ene and the like.

The term "proton acceptor" as used herein means a proton acceptor selected from an organic proton acceptor and inorganic proton acceptor, as defined hereinabove.

The compounds of formula I form salts with suitable therapeutically acceptable inorganic and organic bases. These derived salts possess the same activity as their parent acid and are included within the scope of this invention. The acid is transformed in excellent yield into the corresponding therapeutically acceptable salt by neutralization of said acid with the appropriate inorganic or organic base. The salts are administered usually in the same manner as the parent acid compounds. Suitable inorganic bases to form these salts include, for example, the hydroxides, carbonates or bicarbonates of the therapeutically acceptable alkali metals or alkaline earth metals, for example, sodium, potassium, magnesium, calcium and the like. Suitable organic bases include the following amines: benzylamine; lower mono-, di- and trialkylamines, the alkyl radicals of which contain up to three carbon atoms, such as methylamine, dimethylamine, trimethylamine, ethylamine, di- and triethylamine, methylethylamine, and the like; mono-, di- and trialkanolamines, the alkanol radicals of which contain up to three carbon atoms, for example, mono-, di- and triethanolamine; alkylenediamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methyl-morpholine and N-(2-hydroxyethyl)-piperidine, as well as pyridine. Furthermore, there may be mentioned the corresponding quaternary salts, such as the tetraalkyl (for example tetramethyl), alkyl-alkanol (for example tetramethyl), alkyl-alkanol (for example methyltriethanol and trimethyl-monoethanol) and cyclic ammonium salts, for example the N-methylpyridinium, N-methyl-N-(2-hydroxyethyl)-morpholinium N,N-dimethylmorpholinium, N-methyl-N-(2-hydroxyethyl)-morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula I in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acidic compound of formula I is dissolved in a suitable solvent of either moderate or low polarity, for example, ethanol, methanol, ethyl acetate, diethyl ether or benzene. At least an equivalent amount of the amine corresponding to the desired cation is then added to that solution. If the resulting salt does not precipitate, it can usually be obtained in solid form by addition of a miscible diluent of lower polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula I with an equivalent amount of the corresponding quaternary ammonium hydroxide in water solution, followed by evaporation of the water.

The compounds of this invention and their addition salts with pharmaceutically acceptable organic or inorganic bases may be administered to mammals, for example, man, cattle or rabbits, either alone or in dosage forms, i.e., capsules or tablets, combined with pharmacologically acceptable excipients, see below. Advantageously the compounds of this invention may be given orally. However, the method of administering the present active ingredients of this invention is not to be construed as limited to a particular mode of administration. For example, the compounds may be administered topically directly to the eye in the form of drops of sterile, buffered ophthalmic solution, preferably of pH 7.2–7.6. Also, they may be administered orally in solid form containing such excipients as starch, milk sugar, certain types of clay and so forth. They may also be administered orally in the form of solutions or they may be injected parenterally. For parenteral administration they may be used in the form of a sterile solution, preferably of pH 7.2–7.6, containing a pharmaceutically acceptable buffer.

The dosage of the present therapeutic agents will vary with the form of administration and the particular compound chosen. Furthermore, it will vary with the particular host under treatment. Generally, treatment is initiated with small dosages substantially less than the optimal dose of the compound. Thereafter, the dosage is increased by small increments until efficacy is obtained. In general, the compounds of this invention are most desirably administered at a concentration level that will generally afford effective results without causing any harmful or deleterious side effects. For topical administration a 0.05–0.2% solution may be administered dropwise to the eye. The frequency of instillation varies with the subject under treatment from a drop every two or three days to once daily. For oral or parenteral administration a preferred level of dosage ranges from about 50 mg to about 250 mg per kilo of body weight per day, although aforementioned variations will occur. However, a dosage level that is in the range of from about 100 mg to about 250 mg per kilo of body weight per day is most satisfactory.

Unit dosage forms such as capsules, tablets, pills and the like may contain from about 25 mg to about 500 mg of the active ingredients of this invention, dependent on the type of unit dosage, optionally with a quantity of a pharmaceutically carrier. Thus, for oral administration, capsules can contain from between about 25 mg to about 500 mg of the active ingredients of this invention with or without a pharmaceutical diluent. Tablets, either effervescent or noneffervescent, can contain between about 25 to 500 mg of the active ingredients of this invention together with conventional pharmaceutical carriers. Thus, tablets which may be coated and either effervescent or noneffervescent may be prepared according to the known art. Inert diluents or carriers, for example, magnesium carbonate or lactose, can be used together with conventional disintegrating agents for example, magnesium stearate.

Syrups or elixirs suitable for oral administration can be prepared from water soluble salts, and may advantageously contain glycerol and ethyl alcohol as solvents or preservatives.

The compounds of formula I, or their therapeutically acceptable salts, also can be used in combination with insulin or oral hypoglycemic agents to produce beneficial effect in the treatment of diabetes mellitus. In this instance, commercially available insulin preparations or oral hypoglycemic agents, exemplified by acetohexamide, chlorpropamide, tolazamide, tolbutamide and phenformin, are suitable. The compounds of formula I, or their therapeutically acceptable salts, can be administered sequentially or simultaneously with insulin or the oral hypoglycemic agent. Suitable methods of administration, compositions and doses of the insulin preparation or oral hypoglycemic agent are described in medical textbooks; for instance, "Physicians' Desk Reference," 34 ed., Medical Economics Co., Oradell, N.J., U.S.A., 1980. When used in combination, the compounds of formula I, or their therapeutically acceptable salts, are administered as described previously. The compounds of formula I, or their therapeutically acceptable salts, can be administered with the oral hypoglycemic agent in the form of a pharmaceutical composition comprising effective amounts of each agent.

The aldose reductase inhibiting effects of the compounds of formula I and their pharmaceutically acceptable salts with organic or inorganic bases can be demonstrated by employing an in vitro testing procedure similar to that described by S. Hayman and J. H. Kinoshita, J. Biol. Chem., 240, 877 (1965). In the present case the procedure of Hayman and Kinoshita is modified in that the final chromatography step is omitted in the preparation of the enzyme from bovine lens.

The following results were obtained when the foregoing listed compounds of formula I were evaluated in the above in vitro test.

| Compound of Formula I | | Example In Which Compound Is Prepared | % Inhibition at Different Molar Concentrations (in vitro) | | |
|---|---|---|---|---|---|
| $R^1$ | $R^2$ | | $10^{-5}$ | $10^{-6}$ | $10^{-7}$ |
| COOH | H | 4 | 89 | 65 | 19 |
| COOH | 8-Br | 4 | 81 | 47 | 14 |
| COOH | 6-OH | 4 | 84 | 53 | 16 |
| CON(CH$_3$)—CH$_2$COOH | H | 7 | 22 | | |

Process

The compounds of formula I can be obtained by hydrolyzing a compound of formula II

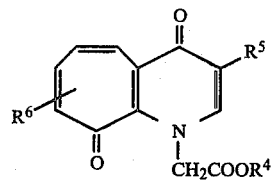

in which $R^4$ is lower alkyl, $R^5$ is COOR$^7$ wherein $R^7$ is lower alkyl and $R^6$ is hydrogen, 8-halo or a leaving group, at position 6, capable of being replaced by a hydroxyl under hydrolytic conditions; or in which $R^4$ is lower alkyl, $R^5$ is CON(R$^3$)CH$_2$COOR$^8$ wherein $R^3$ and $R^8$ each is lower alkyl and $R^6$ is hydrogen or 8-halo. Preferred leaving groups are selected from N-methylacetylamino, acetylamino and halo.

The hydrolysis can be performed most conveniently by employing a base in the presence of sufficient water, followed by acidification of the reaction mixture to yield the desired acid. However, it should be understood that the manner of hydrolysis for the process of this invention is not intended to be limited to basic hydrolysis since hydrolysis is under acidic conditions and other variations, for example treatment with lithium iodide in collidine (see L. F. Fieser and M. Fieser, "Reagents for Organic Synthesis," John Wiley and Sons, Inc., New York, 1969, pp. 615–617), also are applicable. Hydrolysis under acidic conditions is preferred for tert butyl esters.

For acid hydrolysis, a preferred embodiment involves subjecting the corresponding ester to the action of a strong organic or inorganic acid, for example, hydrochloric acid, sulfuric acid, trifluoroacetic acid or p-toluene-sulfonic acid, in the presence of sufficient water to effect hydrolysis. Suitable solvents include water, the lower alkanols and acetic acid. The reaction mixture is maintained at a temperature ranging from 20° to 100° C. or at the reflux temperature of the solvent employed until hydrolysis is complete. Usually a reaction time of 30 minutes to two hours is sufficient.

For basic hydrolysis, a preferred embodiment involves subjecting the ester to the action of a strong base, for example, sodium hydroxide or potassium hydroxide, in the presence of sufficient water to effect hydrolysis of the ester. The hydrolysis is performed using a suitable solvent, for example, methanol ethanol or 2-methoxyethanol. The reaction mixture is maintained at a temperature ranging from 25° to 100° C. or at the reflux temperature of the solvent employed until hydrolysis is complete. Usually from 10 minutes to 6 hours is sufficient. The reaction mixture is then rendered acidic with an acid, for example, acetic acid, hydrochloric acid or sulfuric acid, to release the free acid.

Optionally, if the therapeutically acceptable salt, with an inorganic base, of the compound of formula I is desired, the basic hydrolysis can be effected with a strong base having a physiologically compatible cation, for example Na$^+$, K$^+$ or Ca$^{++}$. In this instance, a sufficient amount of the base is used to give the desired salt and the salt is isolated by evaporating the solvent from the reaction mixture.

With reference to the above starting material of formula II, the compound can be prepared by a process illustrated as follows:

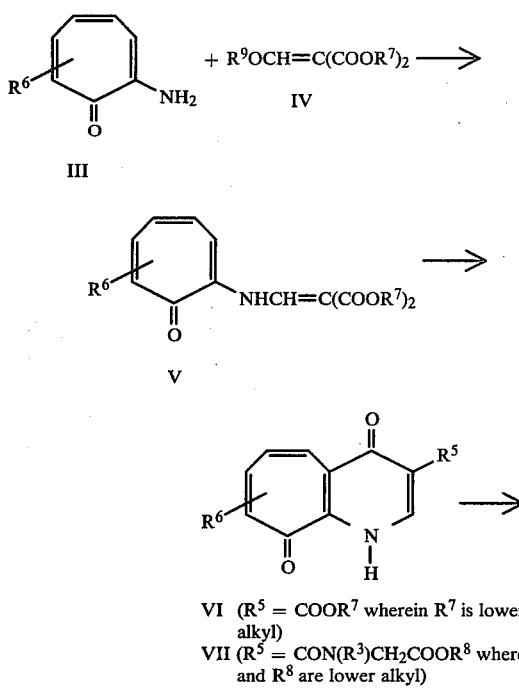

VI ($R^5$ = COOR$^7$ wherein $R^7$ is lower alkyl)
VII ($R^5$ = CON($R^3$)CH$_2$COOR$^8$ wherein $R^3$ and $R^8$ are lower alkyl)

wherein $R^6$ is hydrogen, 8-halo or a leaving group as defined hereinabove, and $R^9$ is lower alkyl.

The aminotropones of formula III are known, for example see T. Nozoe et al., Proc. Japan Acad., 27, 4 and 188 (1951), and F. Pietra, Chem. Rev., 73, 293 (1973), or they can be prepared by known methods.

With reference to the latter reaction scheme, the aminotropone of formula III in which $R^6$ is as defined in the last instance is condensed with a (lower)alkoxymethylenemalonic acid di(lower)alkyl ester of formula IV in which $R^7$ and $R^9$ are lower alkyl, in the presence of an alkali metal lower alkoxide, to obtain the corresponding diester of formula V in which $R^6$ and $R^7$ are as defined herein. This condensation can be accomplished conveniently by heating a mixture of the aminotropone with an excess (preferably five to ten molar equivalents) of the (lower)alkoxymethylenemalonic acid di(lower)alkyl ester at temperatures ranging from 120° to 160° C., preferably 135°–145° C. An inert high boiling solvent can be used for this reaction; however, an excess of the (lower)alkoxymethylenemalonic acid di(lower)alkyl ester is the most practical solvent. The reaction is maintained at the elevated temperature for about one to four hours. Thereafter, the reaction mixture is cooled and the desired diester of formula V is separated from the excess (lower)alkoymethylenemalonic acid di(lower)alkyl ester by standard laboratory means, for instance chromatography. Often, the diester of formula V crystallizes at this point and can be separated by filtration.

Thereafter, the diester of formula V is cyclized at an elevated temperature to give the cycloheptapyridine compound of formula VI in which $R^6$ is as defined herein and $R^5$ is COOR$^7$ wherein $R^7$ is lower alkyl. Although the temperature and reaction time will vary depending on the particular nature of the diester of formula V, it has been found that the cyclization proceeds quite readily at elevated temperatures ranging from 240° to 280° C. Care should be taken to avoid prolonged heating of the reaction mixture which will cause decomposition of the desired product. In most cases, the cyclization is effected at the preceding elevated temperature within ten to 30 minutes. The cyclization is most conveniently done in an inert high boiling solvent. Diphenyl ether (bp 256° C.) and mixtures of diphenyl ether and diphenylmethane are suitable solvents for this purpose.

Thereafter, the cycloheptapyridine compound is transformed into the starting material of formula II. Two different routes are employed depending on the particulary $R^5$ group desired for the starting material of formula II.

By the first route, directed to the preparation of the starting material of formula II in which $R^5$ is COOR$^7$ is lower alkyl, the cycloheptapyridine compound of formula VI is condensed with a haloacetic acid lower alkyl ester in the presence of a proton acceptor to give the ester compound of formula II in which $R^4$ is lower alkyl, $R^5$ is COOR$^7$ wherein $R^7$ is lower alkyl and $R^6$ is as defined herein.

Practical and convenient conditions for effecting the latter condensation include the use of one to two molar equivalents of the proton acceptor. Inorganic proton acceptors, for example, sodium hydride, sodium hydroxide or potassium carbonate, have been found to be suitable proton acceptors. Any solvent, which does not interfer with the reaction, can serve as the reaction medium. Suitable solvents include dimethylformamide, dimethyl sulfoxide, toluene, acetone and tetrahydrofuran. Preferred conditions for effecting the condensation include the use of sodium hydride or potassium carbonate as the proton acceptor and dimethylformamide as the solvent. Although the optimum temperature and reaction time will vary depending on the reactants employed, the reaction is performed generally at 20° to 120° C., or the boiling point of the reaction mixture, for a period of 30 minutes to 48 hours.

By the second route, directed to the preparation of the starting material of formula II in which $R^4$ is lower alkyl, $R^5$ is CON($R^3$)CH$_2$COOR$^8$ wherein $R^3$ and $R^8$ each lower alkyl, and $R^6$ is hydrogen or 8-halo, the cycloheptapyridine compound of formula VI in which $R^5$ is COOR$^7$ wherein $R^7$ is lower alkyl and $R^6$ is hydrogen or 8-halo is hydrolyzed to obtain its corresponding acid. This hydrolysis can be done under either basic or acidic conditions, the conditions having been discussed in more detail hereinbefore with reference to the hydrolysis of the starting material of formula II. The corresponding acid, so obtained, is coupled with an amino acid of the formula NH($R^3$)CH$_2$COOR$^8$ wherein $R^3$ and $R^8$ each is lower alkyl to give the compound of formula VII in which $R^5$ is CON($R^3$)CH$_2$COOR$^8$ wherein $R^3$ and $R^8$ each is lower alkyl and $R^6$ is hydrogen or 8-halo. The coupling is done preferably by the "carboxyl activation" coupling procedure. Descriptions of carboxy-activating groups are found in general textbooks of peptide chemistry; for example K. D. Kopple, "Peptides and Amino Acids," W. A. Benjamin, Inc., New York, 1966, pp. 45–51, and E. Schröder and K. Lübke, "The Peptides;" Vol. 1, Academic Press, New York, 1965, pp. 77–128. Examples of the activated form of the terminal carboxyl are the acid chloride, acid bromide, anhydride, azide, activated ester, or O-acyl urea of a dialkylcarbodiimide. A preferred activated form of the carboxyl is the acid chloride. Thereafter, the compound of formula VII is condensed with a haloacetic acid lower alkyl ester in the presence of a proton acceptor to give the starting material of formula II in which $R^4$ is lower alkyl, $R^5$ is $CON(R^3)CH_2COOR^8$ where $R^3$ and $R^8$ each is lower alkyl and $R^6$ is hydrogen or 8-halo. This condensation is performed in the same manner as the previously described condensation of the compound of formula VI with a haloacetic acid lower alkyl ester.

The following examples illustrate further this invention.

EXAMPLE 1a

2-Amino-5-(N-methylacetylamino)-2,4,6-cycloheptatrien-1-one

A stirred mixture of 5-(acetylamino)-2-hydroxy-2,4,6-cycloheptatrien-1-one (148 g), described by T. Nozoe et al., Proc. Japan Acad., 27, 188 (1951), anhydrous potassium carbonate (300 g), dimethyl sulfate (300 g) and 2-butanone (3 l) was heated at reflux for 20 hr. The hot mixture was filtered and the filtrate was set aside. The collected solid was mixed with fresh quantities of potassium carbonate (300 g), dimethyl sulfate (300 g) and 2-butanone (3 l). The resulting mixture was heated at reflux for 20 hr and filtered while still hot. The combined filtrates were evaporated to dryness. The residue was subjected to chromatography on silica gel using chloroform:methanol (19:1) as the eluant. The pure fractions were pooled giving 2-methoxy-5-(N-methylacetylamino)-2,4,6-cycloheptatrien-1-one (56 g); mp 116°–118° C.; nmr (DMSO-$d_6$) δ1.45(s, 3H), 3.2 (s, 3H), 3.95 (s, 3H), 6.5–7.2 (m, 4H), uv λ max (MeOH) 324 nm (ϵ10,835), 230 (22,940).

The latter compound (10 g) was dissolved in methanol (100 ml) saturated with anhydrous ammonia. The mixture was heated in a pressure bottle at 80° C. for one hr. The mixture was evaporated to dryness to yield the title compound; mp 203–205° C.; nmr (DMSO-$d_6$) δ1.75 (s, 3H), 3.1 (s, 3H), 5.85 & 7.15 (d, 4H), 7.6 (broad, 2H); ir (Nujol*) 3360, 3120, 1635, 1525 cm$^{-1}$; uv λ max (MeOH) 343 nm (ϵ14,690), 273 (4,520), 243 (24,160) with shoulders at 263 and 237 nm.

*Nujol is a trademark for a brand of white mineral oil

EXAMPLE 1b

2-Amino-5-chloro-2,4,6-cycloheptatrien-1-one

5-Chlorotropolone [40 g, described by T. Nozoe et al., Proc. Japan Acad., 27, 4(1951)], dimethyl sulfate (60 ml), anhydrous potassium carbonate (40 g) and 2-butanone (550 ml) were heated at reflux for 1.5 hr. The cooled reaction mixture was filtered and the filtrate was evaporated to dryness. The residue was triturated with diethyl ether and 5-chloro-2-methoxy-2,4,6-cycloheptatrien-1-one, mp 124°–126° C., nmr (CDCl$_3$) δ3.9 (s, 3H), 7.0 (m, 4H), was isolated by filtration. The residue obtained by evaporation of the filtrate, was purified by column chromatography over silica gel using chloroform-methanol (49:1) as the eluant. Pooling of the appropriate fractions gave another 2.6 g of 5-chloro-2-methoxy-2,4,6-cycloheptatrien-1-one.

The latter compound (5 g) was dissolved in methanol (100 ml) saturated with anhydrous ammonia. The mixture was heated in a pressure bottle at 80° C. for one hr. The mixture was evaporated to dryness and a residue was purified by chromatography on silica gel using chloroform-methanol (19:1) as the eluant. The appropriate fractions were pooled to give 4.07 g of the title compound, nmr (DMSO-$d_6$) δ6.8 & 7.35 (2d, 4H), 7.65 (broad, 2H).

EXAMPLE 1c

2-Amino-7-bromo-2,4,6-cycloheptatrien-1-one

A solution of $CuSO_4.5H_2O$ (96 g) in water (600 ml) was added dropwise to a stirred solution of tropolone (100 g) in methanol (1000 ml) at 25° C. After standing at 25° C. for 30 min, the mixture was filtered. The collected solid, i.e. the copper complex of tropolone, was washed several times with water and air dried. The infrared spectrum of the complex in (Nujol*) showed bands at 1515, 1545, 1235 cm$^{-1}$.

*Trademark

Bromine (104 g) was added dropwise to a stirred suspension of the complex (98 g) and anhydrous sodium acetate (106.6 g, 1.3 mole) in chloroform (6 l) at 25° C. The mixture was allowed to stand at 25° C. for 30 min. The mixture was filtered. Excess copper complex in the filtrate was removed by treatment with hydrogen sulfide gas. The filtrate then was treated with gaseous hydrogen bromide. The resulting precipitate was collected and dissolved in water. The pH of the solution was adjusted to 3.5–4 with ammonia and the solution was extracted with chloroform. Evaporation of the chloroform extract gave 3-bromo-2-hydroxy-2,4,6-cycloheptatrien-1-one, nmr (DMSO-$d_6$) δ6.75–8.3 (4H, m), 8.3 (broad, 1H).

A stirred mixture of the latter compound (50 g), anhydrous potassium carbonate (100 g), dimethyl sulfate (80 g) and 2-butanone (400 ml) was heated at reflux for 3.5 hr, cooled and filtered. The filtrate was evaporated to dryness. The residue was purified by chromatography on silica gel using benzene-acetone (9:1) as the eluant. The first fractions gave about 1 g of 3,7-dibromo-2-methoxy-2,4,6-cycloheptatrien-1-one containing a small amount of the 3,5,7-tribromoanalog. Subsequent fractions yielded 12 g of 7-bromo-2-methoxy-2,4,6-cycloheptatrien-1-one; mp 74°–75° C.; nmr (DMSO-$d_6$) δ3.8 (s, 3H), 7.0 (m, 4H).

The latter compound (4 g) was dissolved in methanol (50 ml) saturated with anhydrous ammonia. The mixture was heated in a pressure bottle at 80° C. for one hr. The mixture was evaporated to dryness. The residue was purified by chromatography on silica gel using chloroform-methanol (49:1) as the eluant. Pooling of the appropriate fractions gave 3.6 g of the title compound; mp 133°–135° C.; nmr (DMSO-$d_6$) δ7.1 (m, 4H), 7.85 (broad, 2H).

EXAMPLE 2

4,9-Dihydro-4,9-dioxo-1H-cyclohepta[b]pyridine-3-carboxylic Acid Ethyl Ester

A mixture of 2-amino-2,4,6-cycloheptatrien-1-one (2 g), described by W. Von E. Doering and L. H. Knox, J. Amer. Chem. Soc., 73, 828 (1951), and diethyl ethoxymethylenemalonate (20 ml) was heated at 140° C. for 2 hr. The reaction was cooled and subjected to chromatography on silica gel using dichloromethane-ethyl acetate (4:1) as the eluant. The pure fractions were pooled to give 4.13 g of 2-[(7-oxo-1,3,5-cycloheptatrien-1-yl)aminomethylene]-propanedioic acid diethyl ester; mp 66°–68° C.; nmr (CDCl$_3$) δ1.35 (m, 6H), 4.35 (m, 2H), 7.35 (m, 5H), 8.4 (d, 1H), 11.4 (broad, 1H); ir (CHCl$_3$) 3230, 1700, 1665, 1580 cm$^{-1}$; uv λ max (MeOH) 356 nm (ϵ13,770), 292 (9,880), 277 (10,680), 213 (17,020) with shoulders at 338 and 236 nm.

The latter compound (5 g) was added to 100 ml of boiling diphenyl ether. After 10 minutes, the reaction mixture was cooled and diluted with chloroform. Thin layer chromatography on silica gel plates using chloroform-methanol (19:1) as the mobile phase indicated two main products (Rf 0.6 and Rf 0.5). The same thermal cyclization was repeated with three more 5 g portions. The pooled reaction mixtures were subjected to chromatography on silica gel using chloroform-methanol (99:1) as the eluant. The two main products thus were separated. The product with Rf 0.6 (7.2 g) was identified as cyclohepta[b]pyrrole-3-carboxylic acid ethyl ester; mp 65°–67° C.; nmr (CDCl$_3$) δ1.4 (t, 3H), 4.4 (q, 2H), 7.8–9.6 (m, 6H), a byproduct. The product with Rf 0.5 (4.7 g, after recrystallization from ethanol) was identified as the title compound; mp 188°–190° C.; nmr (CDCl$_3$) δ1.4 (t, 3H), 4.4 (q, 2H), 7.0–8.7 (m, 6H); ir (Nujol*) 3100, 1717 cm$^{-1}$; uv λ max (MeOH) 3.47 nm (ε13,240), 238 (20,330); Anal Calcd for C$_{13}$H$_{11}$NO$_4$: C, 63.67% H, 4.52% N, 5.71%; Found C, 63.51% H, 4.58% N, 5.63%.

*Trademark

In the same manner, but replacing 2-amino-2,4,6-cycloheptatrien-1-one with an equivalent amount of 2-amino-5-(N-methylacetylamino)-2,4,6-cycloheptatrien-1-one, described in example 1a, and conducting the thermal cyclization for eight minutes, 4,9-dihydro-6-(N-methylacetylamino)-4,9-dioxo-1H-cyclohepta[b]pyridine-3-carboxylic acid ethyl ester was obtained. The latter compound had mp>250° C.; nmr (DMSO-d$_6$) δ1.3 (t, 3H), 1.46 (s, 3H), 3.2 (s, 3H), 4.2 (9, 2H), 7.7 (m, 4H), 12.0 (broad, 1H); ir (Nujol*) 3220, 1705, 1660, 1584; uv λ max (MeOH) 232 nm (ε20,195); Anal Calcd for C$_{16}$H$_{16}$N$_2$O$_5$: C, 60.76% H, 5.10% N, 8.86%; Found: C, 60.83% H, 5.21% N, 8.96. The compound was obtained via the intermediate 2-[(4-N-methylacetylamino)-7-oxo-1,3,5-cycloheptatrien-1-yl]aminomethylene propanedioic acid diethyl ester; mp 110°–112° C.; nmr (CDCl$_3$) δ1.35 (m, 6H), 1.95 (s, 3H), 3.75 (s, 3H), 4.3 (m, 4H), 7.15 (m, 4H), 8.35 (d, 1H).

*Trademark

Likewise, replacement with 5-(acetylamino)-2-amino-2,4,6-cycloheptatrien-1-one, prepared from 5-(acetylamino)-2-methoxy-2,4,6-cycloheptatrien-1-one and anhydrous ammonia according to the procedure of example 1, gave 6-(acetylamino)-4,9-dihydro-4,9-dioxo-1H-cyclohepta[b]pyridine-3-carboxylic ethyl ester.

Likewise, replacement with 2-amino-5-chloro-2,4,6-cycloheptatrien-1-one, described in example 1b, and a thermal cyclization time of 10 min, gave 6-chloro-4,9-dihydro-4,9-dioxo-1H-cyclohepta[b]pyridine-3-carboxylic acid ethyl ester; mp 235°–237° C.; nmr (DMSO-d$_6$) δ1.3 (t, 3H), 4.2 (q, 2H), 7.6 (m, 4H), 12.0 (s, 1H); ir (KBr) 3050, 1722, 1595, 1525 cm$^{-1}$; uv λ max (MeOH) 353 nm (ε14,735), 225 (20,675); via the intermediate 2-[(4-chloro-7-oxo-1,3,5-cycloheptatrien-1-yl)aminomethylene]propanedioic acid diethyl ester; mp 138°–140° C.; nmr (CDCl$_3$) δ1.35 (m, 6H), 4.3 (m, 4H), 7.2 (m, 4H), 8.35 (d, 1H), 11.5 (d, 1H); ir (CHCl$_3$) 3210, 1710, 1695, 1565 cm$^{-1}$; uv λ max (MeOH) 280 nm (ε10,920), 241 (17,090), 216 (20,510).

Likewise, replacement with 2-amino-7-bromo-2,4,6-cycloheptatrien-1-one, described in example 1c, and a thermal cyclization time of 4 min, gave 8-bromo-4,9-dihydro-4,9-dioxo-1H-cyclohepta[b]pyridine-3-caboxylic acid ethyl ester; mp 245° C. (dec); nmr (DMSO-d$_6$) δ1.27 (t, 3H), 4.2 (q, 2H), 7.0 (m, 1H), 8.35 (m, 3H) and about 8.35 (m, 1H); via the intermediate 2-[(6-bromo-7-oxo-1,3,5-cycloheptatrien-1-yl)aminomethylene]-propanedioic acid diethyl ester; mp 153°–155° C.; nmr (CDCl$_3$) δ1.35 (m, 6H), 4.3 (m, 4H), 7.6 (m, 5H).

EXAMPLE 3

3-(Ethoxycarbonyl)-4,9-dihydro-4,9-dioxo-1H-cyclohepta[b]pyridine-1-acetic Acid Ethyl Ester (II; R$^4$=C$_2$H$_5$, R$^5$=COOC$_2$H$_5$ and R$^6$=H)

A mixture of 4,9-dihydro-4,9-dioxo-1H-cyclohepta[b]pyridine-3-carboxylic acid ethyl ester (1 g, described in example 2), potassium carbonate (1 g) and ethyl bromoacetate (1 g) in dimethylformamide (DMF, 50 ml) was stirred at 25° C. for 5 hr. The reaction mixture was diluted with water and extracted with chloroform. The chloroform extract was evaporated to dryness. The residue was purified by chromatography on silica gel using chloroform-methanol (99:1) as the eluant. The appropriate fractions were pooled and crystallized from acetone to give the title compound; mp 152°–154° C.; nmr (CDCl$_3$) δ1.3 (t, 6H), 4.3 (m, 4H), 4.85 (s, 2H), 7.0 (m, 3H), 8.2 (m, 2H); ir (CHCl$_3$) 1740, 1730, 1690, 1630 cm$^{-1}$; uv λ max (MeOH) 349 nm (ε12,625), 235 (18,760), 212 (25,070); Anal Calcd for C$_{17}$H$_{17}$NO$_6$: C, 61.63% H, 5.17% N, 4.23% Found: C, 61.67% H, 5.23% N, 4.25%.

In the same manner, but replacing 4,9-dihydro-4,9-dioxo-1H-cyclohepta[b]pyridine-3-carboxylic acid ethyl ester with an equivalent amount of 4,9-dihydro-6-(N-methylacetlyamino)-4,9-dioxo-1H-cyclohepta[b]pyridine-3-carboxylic acid ethyl ester, described in example 2, 3-(ethoxycarbonyl)-4,9-dihydro-6-(N-methylacetylamino)-4,9-dioxo-1H-cyclohepta[b]pyridine-1-acetic acid ethyl ester (I; R$^4$=C$_2$H$_5$, R$^5$=COOC$_2$H$_5$ and R$^6$=6-N(CH$_3$)COCH$_3$); nmr (CDCl$_3$) δ1.35 (m, 6H), 2.03 (s, 3H), 3.25 (s, 3H), 4.3 (m, 4H), 4.9 (s, 2H), 7.5 (m, 4H), was obtained.

Likewise, replacement with 6-(acetylamino)-4,9-dihydro-4,9-dioxo-1H-cyclohepta[b]pyridine-3-carboxylic acid ethyl ester, described in example 2, gives 6-(acetylamino)-3-(ethoxycarbonyl)-4,9-dihydro-4,9-dioxo-1H-cyclohepta[b]pyridine-1-acetic acid ethyl ester (II; R$^4$=C$_2$H$_5$, R$^5$=COOC$_2$H$_5$ and R$^6$=6-NHCOCH$_3$).

Likewise, replacement with 6-chloro-4,9-dihydro-4,9-dioxo-1H-cyclohepta[b]pyridine-3-carboxylic acid ethyl ester, described in example 2, gives 6-chloro-3-(ethoxycarbonyl)-4,9-dihydro-4,9-dioxo-1H-cyclohepta[b]pyridine-1-acetic acid ethyl ester (II; R$^4$=C$_2$H$_5$, R$^5$=COOC$_2$H$_5$ and R$^6$=6-Cl).

Likewise, replacement with 8-bromo-4,9-dihydro-4,9-dioxo-1H-cyclohepta[b]pyridine-3-carboxylic acid ethyl ester, described in example 2, gives 8-bromo-3-(ethoxycarbonyl)-4,9-dihydro-4,9-dioxo-1H-cyclohepta[b]pyridine-1-acetic acid ethyl ester (II; R$^4$=C$_2$H$_5$, R$^5$=COOC$_2$H$_5$ and R$^6$=8-Br); mp 100°–102° C.; nmr (CDCl$_3$) δ1.3 (m, 6H), 4.3 (m, 4H), 4.9 (s, 2H), 7.5 (m, 4H); ir (CHCl$_3$) 1745, 1698, 1635 cm$^{-1}$; uv λ max (MeOH) 352 nm (ε11,770), 291 (9,510), 244 (13,540), 215 (24,080).

EXAMPLE 4

3-Carboxy-4,9-dihydro-4,9-dioxo-1H-cyclohepta[b]pyridine-1-acetic Acid (I; R$^1$=COOH and R$^2$=H)

A suspension of 3-(ethoxycarbonyl)-4,9-dihydro-4,9-dioxo-1H-cyclohepta[b]pyridine-1-acetic acid ethyl ester (2.2 g, described in example 3) in 5% aqueous HCl (v/v, 90 ml) was heated at reflux for 2 hr. The precipitate was collected by filtration and washed with water to give 1.4 g of the title compound; mp>250° C. (after recrystallization from ethanol); nmr (DMSO-d$_6$) δ5.1 (s, 2H), 7.2 (m, 3H), 7.95 (m, 1H), 8.95 (s, 1H); ir (Nujol*) 2850, 1730, 1707, 1640 cm$^{-1}$; uv λ max (MeOH) 344 nm (ε13,030), 235 (19,030); Anal Calcd for C$_{13}$H$_9$NO$_6$: C, 56.73% H, 3.30% N, 5.09%; Found: C, 56.76% H, 3.40% N, 5.05%.

*Trademark

In the same manner, but replacing 3-(ethoxycarbonyl)4,9-dihydro-4,9-dioxo-1H-cyclohepta[b]pyridine-1-acetic acid ethyl ester with an equivalent amount of either 3-(ethoxycarbonyl)-4,9-dihydro-6-(N-methylacetylamino)-4,9-dihydro-1H-cyclohepta[b]pyridine-1-acetic acid ethyl ester, 6-(acetylamino)-4,9-dihydro-4,9-dioxo-1H-cyclohepta[b]pyridine-3-carboxylic acid ethyl ester or 6-chloro-3-(ethoxycarbonyl)-4,9-dihydro-4,9-dioxo-1H-cyclohepta[b]pyridine-1-acetic acid ethyl ester, gave the same product, namely 3-carboxy-4,9-dihydro-6-hydroxy-4,9-dioxo-1H-cyclohepta[b]pyridine-1-acetic acid (I; R$^1$=COOH and R$^2$=6-OH); mp>250° C. (after recrytallization from acetone); nmr (DMSO-d$_6$) δ5.5 (s, 2H), 7.5 (d, H), 8.3 (d, 1H),8.9 (s, 1H); ir (Nujol*) 2900, 1743, 1694 cm$^{-1}$; uv λ max (MeOH) 341 nm (ε12,500), 237 (32,000); Anal Calcd for C$_{13}$H$_9$NO$_7$: C, 53.62% H, 3.12% N, 4.81%; Found: C, 53.22% H, 3.05% N, 4.73%.

Likewise, replacement with 8-bromo-3-(ethoxycarbonyl)-4,9-dihydro-4,9-dioxo-1H-cyclohepta[b]pyridine-1-acetic acid ether ester, described in example 3, gave 8-bromo-3-carboxy-4,9-dihydro-4,9-dioxo-1H-cyclohepta[b]pyridine-1-acetic acid (I; R$^1$=COOH and R$^2$=8-Br); mp 173°-175° C. (after recrystallization from acetone-water); nmr (DMSO-d$_6$) δ5.1 (s, 2H), 7.11 (m, 3H), 8.95 (s, 1H); ir (Nujol*) 3000, 1735, 1615 cm$^{-1}$; uv λ max (MeOH) 347 nm (ε11,190); 244 (13,560); 216 (22,485); Anal Calcd for C$_{13}$H$_8$BrNO$_6$: C, 44.09% H, 2.27% N, 3.96%; Found: C, 43.35% H, 2.25% N, 3.82%.

*Trademark

EXAMPLE 5

4,9-Dihydro-4,9-dioxo-1H-cyclohepta[b]pyridine-3-carboxylic Acid

A mixture of 4,9-dihydro-4,9-dioxo-1H-cyclohepta[b]pyridine-3-carboxylic acid ethyl ester (5.5 g, described in example 2) and 5% aqueous HCl (v/v, 100 ml) was heated at reflux for 2 hr. The reaction mixture was cooled. The precipitate was collected and washed with water and acetone to give 4.38 g of the title compound, nmr (DMSO-d$_6$) δ7.5 (m, 4H), 8.55 (s, 1H), 8.95 (broad, 1H), 10.8 (s, 1H).

In the same manner, but replacing 4,9-dihydro-4,9-dioxo-1H-cyclohepta[b]pyridine-3-carboxylic acid ethyl ester with an equivalent amount of 8-bromo-4,9-dihydro-4,9-dioxo-1H-cyclohepta[b]pyridine-3-carboxylic acid ethyl ester, described in example 2, 8-bromo-4,9-dihydro-4,9-dioxo-1H-cyclohepta[b]pyridine-3-carboxylic acid is obtained.

EXAMPLE 6

3-{[N-(Methoxycarbonylmethyl)-N-methylamino]carbonyl}-4,9-dihydro-4,9-dioxo-1H-cyclohepta[b]pyridine-1-acetic Acid Ethyl Ester (II; R$^4$=C$_2$H$_5$), R$^5$=CON(CH$_3$)CH$_2$COOCH$_3$ and R$^6$=H)

A mixture of 4,9-dihydro-4,9-dioxo-1H-cyclohepta[b]pyridine-3-carboxylic acid (2.3 g, described in example 5) and thionyl chloride (25 ml) was heated at reflux for 15 min. The solution was evaporated to dryness. The residue (i.e the corresponding acid chloride) was dissolved in benzene and the solution was evaporated to dryness to remove traces of thionyl chloride. A suspension of N-methylglycine methyl ester hydrochloride (4 g) in pyridine (50 ml) was added to the acid chloride. The reaction mixture was kept at 25° C. for 2 hr and then at 75°-80° C. for 10 min. The mixture was diluted with water and extracted with chloroform. The organic extract was evaporated to dryness. The residue was purified by chromatography on silica gel using chloroform-methanol (97:3) as the eluant. The fractions were pooled to give 0.5 g of starting material in one lot and in another lot 1.5 g of N-[(4,9-dihydro-4,9-dioxo-1H-cyclohepta[b]pyridin-3-yl)carbonyl]-N-methylglycine methyl ester; nmr (CDCl$_3$) δ3.0 (d, 3H), 3.7 (d, 3H), 4.2 (d, 2H), 7.2 (m, 3H), 8.2 (m, 2H); ir (CHCl$_3$) 3275, 1731, 1640, 1618 cm$^{-1}$; uv λ max (MeOH) 358 nm (ε10,730), 342 (10,910), 236 (18,390).

A mixture of the latter compound (2.3 g), potassium carbonate (2.5 g), ethyl bromoacetate (2.5 g) and DMF (100 ml) was kept at 25° C. for 4 hr. The mixture was diluted with water and extracted with chloroform. The chloroform extract was evaporated to dryness. The residue was subjected to chromatrography on silica gel using chloroform-methanol (20:1) as the eluate. The pure fractions were combined to give 2.2 g of the title compound; nmr (CDCl$_3$) δ1.3 (m, 3H), 3.1 (d, 3H), 3.8 (d, 3H), 4.2 (m, 4H), 4.9 (d, 2H), 6.8–8.2 (m, 5H); ir (CHCl$_3$) 1745, 1637, 1600 cm$^{-1}$; uv λ max (MeOH) 342 nm (ε10,333), 239 (17,520).

EXAMPLE 7

3-{[N-(Carboxymethyl)-N-methylamino]carbonyl}-4,9-dihydro-4,9-dioxo-1H-cyclohepta[b]pyridine-1-acetic Acid Disodium Salt (Disodium salt of I; R$^1$=CON(CH$_3$)CH$_2$COOH and R$^2$=H)

A mixture of 3-{[N-(methoxycarbonylmethyl)-N-methylamino]carbonyl}-4,9-dihydro-4,9-dioxo-1H-cyclohepta[b]pyridine-1-acetic acid ethyl ester (2.36 g, described in example 6) and 2% aqueous sodium hydroxide (w/v, 25 ml) was stirred at 25° C. for 4 hr. Evaporation of the reaction mixture gave the title disodium salt. The salt decomposed in the presence of acid. The salt had mp>250° C.; nmr (D$_2$O) δ3.0 (d, 3H), 4.0 (d, 2H), 4.7 (s, 2H), 6.8–8.3 (m, 5H); ir (Nujol*) 3400, 3150, 1610 cm$^{-1}$ (with inflections at 1625 and 1585 cm$^{-1}$); uv λ max (MeOH) 340 nm (ε7,390), 237 (13,000); Anal Calcd for C$_{16}$H$_{12}$N$_2$O$_7$Na$_2$.3H$_2$O: C, 43.24% H, 4.08% N, 6.05%; Found: C, 42.76% H, 3.57%, N, 7.18%.

*Trademark

By following serially the procedures of examples 6 and 7, but replacing 4,9-dihydro-4,9-dioxo-1H-cyclohepta[b]pyridine-3-carboxylic acid, with 8-bromo-4,9-dihydro-4,9-dioxo-1H-cyclohepta[b]pyridine-3-carboxylic acid, described in example 5, 6-bromo-3-{[N-(carboxymethyl)-N-methylamino]carbonyl}-4,9-dihydro-4,9-dioxo-1H-cyclohepta[b]pyridine-1-acetic acid disodium salt is obtained.

We claim:

1. A compound of formula I

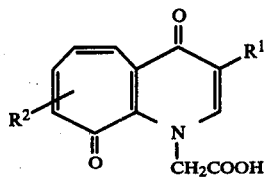

in which R¹ is COOH and R² is hydrogen, 8-halo or 6-hydroxy; or R¹ is CON(R³)—CH₂COOH wherein R³ is lower alkyl and R² is hydrogen or 8-halo; or a therapeutically acceptable salt thereof with an organic or inorganic base.

2. The compound of claim 1 having the formula I in which R¹ is COOH and R² is hydrogen, 8-halo or 6-hydroxy, or R¹ si CON(CH₃)CH₂COOH and R² is hydrogen, or a therapeutically acceptable salt thereof with an organic or inorganic base.

3. The compound of claim 1 having the formula I in which R¹ is COOH and R² is hydrogen, 8-bromo or 6-hydroxy, or a therapeutically acceptable salt thereof with an organic or inorganic base.

4. 3-Carboxy-4,9-dihydro-4,9-dioxo-1H-cyclohepta[b]pyridine-1-acetic acid, as claimed in claim 1.

5. 3-Carboxy-4,9-dihydro-6-hydroxy-4,9-dioxo-1H-cyclohepta[b]pyridine-1-acetic acid, as claimed in claim 1.

6. 8-Bromo-3-carboxy-4,9-dihydro-4,9-dioxo-1H-cyclohepta[b]pyridine-1-acetic acid, as claimed in claim 1.

7. 3-[N-(Carboxymethyl)-N-methylamino]carbonyl-4,9-dihydro-4,9-dioxo-1H-cyclohepta[b]pyridine-1-acetic acid disodium salt, as claimed in claim 1.

8. A pharmaceutical composition for preventing or relieving diabetic complications, selected from neuropathy, nephropathy, retinopathy and cataracts, in a diabetic mammal, which comprises a therapeutically effective amount of a compound of claim 1, or a therapeutically acceptable salt thereof with an organic or inorganic base, and a pharmaceutically acceptable carrier.

9. A method of preventing or relieving a diabetic complication selected from neuropathy, nephropathy, retinopathy and cataracts, in a diabetic mammal, which comprises administering to said mammal an alleviating or prophylactic amount of a composition of claim 8.

* * * * *